United States Patent
Chen et al.

(10) Patent No.: US 10,072,244 B2
(45) Date of Patent: Sep. 11, 2018

(54) METHOD FOR PREPARING HETEROGENETIC CORNEAL MATERIAL

(71) Applicant: YOUVISION BIOTECH CO., LTD., Guangzhou (CN)

(72) Inventors: Wei Chen, Wenzhou (CN); Qinxiang Zhen, Wenzhou (CN); Yongliang Lin, Guangzhou (CN)

(73) Assignee: YOUVISION BIOTECH CO., LTD., Guangzhou (CN)

( * ) Notice: Subject to any disclaimer, the term of this patent is extended or adjusted under 35 U.S.C. 154(b) by 83 days.

(21) Appl. No.: 15/033,444

(22) PCT Filed: Jan. 27, 2014

(86) PCT No.: PCT/CN2014/071544
§ 371 (c)(1),
(2) Date: Apr. 29, 2016

(87) PCT Pub. No.: WO2015/062177
PCT Pub. Date: May 7, 2015

(65) Prior Publication Data
US 2016/0251617 A1  Sep. 1, 2016

(30) Foreign Application Priority Data
Oct. 31, 2013 (CN) .......................... 2013 1 0527550

(51) Int. Cl.
*C12N 5/079* (2010.01)
*A61L 27/36* (2006.01)

(52) U.S. Cl.
CPC ........ *C12N 5/0621* (2013.01); *A61L 27/3604* (2013.01); *A61L 27/3683* (2013.01); *A61L 27/3687* (2013.01); *A61L 2430/16* (2013.01); *A61L 2430/40* (2013.01)

(58) Field of Classification Search
None
See application file for complete search history.

(56) References Cited

U.S. PATENT DOCUMENTS

2007/0142908 A1* 6/2007 Xu .......................... A01N 1/00
623/5.16

FOREIGN PATENT DOCUMENTS

| CN | 1692891 A | 11/2005 |
|---|---|---|
| CN | 1985778 A | 6/2007 |
| CN | 2917585 | 7/2007 |
| CN | 100386061 | 5/2008 |
| CN | 101590292 A | 12/2009 |
| JP | 2009285155 A | 12/2009 |
| JP | 2011526510 A | 10/2011 |
| JP | 2013544593 A | 12/2013 |
| WO | 2013051722 A1 | 4/2013 |

OTHER PUBLICATIONS

English Translation of CN 1692891, 16 pgs created Jan. 2017.*
English Translation of CN 2917585, 9 pgs created Jan. 2017.*
First Office Action for Priority Chinese Patent Application No. 201310527550.4, dated Jun. 25, 2014.
International Search Report and Written Opinion for PCT/CN2014/071544 dated Jul. 22, 2014.
Office Action (Notice of Grounds for Rejection) for corresponding Japanese Patent Application No. 2016-550913, dated Mar. 28, 2017.
Office Action for corresponding Korean Patent Application No. 10-2016-7014289, dated Aug. 7, 2017.
Second Office Action for Priority Chinese Patent Application No. 201310527550.4, dated Feb. 25, 2015.
The exteneded European Search Report and Written Opinion for corresponding European Patent Application No. 14857562.4, dated Jun. 2, 2017.

* cited by examiner

*Primary Examiner* — Thane Underdahl
(74) *Attorney, Agent, or Firm* — Platinum Intellectual Property LLP

(57) ABSTRACT

Disclosed is a method for preparing a heterogenous corneal material, wherein during the whole preparation process, different concentrations of glycerol are used to achieve that the heterogenous corneal graft has the transparent, properties of no viruses and cells; resistance to degradation and immunogenicity of collagen can be further reduced by collagen cross-linking; and under the whole eye saving, cross-linkers 1-(3-dimethylaminopropyl)-3-ethylcarbodiimide (EDC) and N-hydroxy sulfosuccinimide (NHS) are used for cross-linking, thus enabling the form thereof to be closer to that of a fresh cornea and improving biomechanical properties thereof. The method can prepare a heterogenous corneal material with a high transparency, a low immunogenicity and a good bioactivity and biocompatibility, and can maintain that the three-dimensional structure of collagen is close to that of a fresh cornea. The corneal material prepared by the method is improved in both saving of fibre structure of corneal collagen and transparent performance after transplantation and can be widely used in the medical field.

6 Claims, No Drawings

METHOD FOR PREPARING HETEROGENETIC CORNEAL MATERIAL

TECHNICAL FIELD

The present disclosure relates to the field of medicine, and more particularly, it relates to a method for preparing heterogenetic material that can be directly applied in lamellar keratoplasty.

BACKGROUND

Cornea is a transparent membrane located at the front of the eyeball wall, occupying about the first ⅙ of the fiber wall. Cornea takes a circular shape when viewed from behind and a transverse oval shape when viewed from the front. Cornea is the transparent part located at the most front part of the eyeball, and covers the iris, the pupil, and the anterior chamber. It provides most of the refractive power to the eyeball and facilitates correct focus of light on the retina together with the refractive power of the crystalline lens.

Meanwhile, corneal blindness due to loss of corneal transparency is a main cause of vision loss, only second to vision loss caused by cataract. Ocular trauma and corneal ulcers cause blindness to 1.5-2 million people each year. The only effective treatment for this kind of blindness is human corneal transplantation (also called "keratoplasty").

Currently, there is a huge gap between the demand and supply of cornea material in the market. Under the circumstances that allogenic cornea is so lacking and the situation is difficult to change in the short term, people have made various efforts to develop alternative new materials to address the problem of cornea shortage.

New materials that have been reported and verified include mainly biological materials and heterogenetic corneal materials. According to the prior reports, the biomaterials have unsatisfactory tissue compatibility and cannot be used in large scale. In comparison, the heterogenetic corneal materials have broader application prospects. Current technologies focus on removing cells in heterogenetic cornea by use of a protease (trypsin) or phospholipase A2 and other chemical means.

The problem is that these enzymes also have an impact on collagen structure, and thus cause a certain degree of inhibition on the growth of corneal cells after transplantation. Prior literature also indicated a major problem in heterogenetic corneal materials, i.e., graft opacification in the early post-transplantation stage. Therefore, there is still large room for the optimization of the specific treatment methods and preparation methods above.

SUMMARY OF THE INVENTION

Therefore, to mitigate the deficiency of the prior art, one object of the present disclosure is to provide a method for preparing a heterogenetic corneal material, which can prepare heterogenetic corneal materials with extremely high transparency, low immunogenicity, good biological activity, and good biocompatibility. The heterogenetic corneal material as prepared herein has a collagen three-dimensional structure that is similar to a fresh cornea, and further reduces the immunogenicity and degradation of collagen by collagen crosslinking.

Therefore, the present disclosure provides a technical solution comprising the following successive steps:

Step I. Preparation: Eyeballs obtained within four hours after the death of the animal can be used for heterogenetic corneal material. The whole eyeball may be washed with 2% povidone-iodine and 0.9% saline solution in sequence. Then, fascia muscles around the eyeball may be cut off, and the whole eyeball may be washed again with 2% povidone-iodine and 0.9% saline solution in sequence.

Step II. Sterilization: The whole eyeball may be immerged into 10 ml 50% high-glucose solution containing 40 mg of tobramycin for at least 20 minutes and then washed with at 0.9% saline.

Step III. Cell inactivation: The eyeball in whole may be immerged into a solution for sealed preservation with gradual cooling during the preservation process at a temperature drop rate of 2 to 3° C./min, and eventually subjected to long-term preservation of at least four weeks at a temperature of −78° C. The solution comprises 85% to 95% of glycerol and 5% to 15% of a buffer solution.

Step IV. Virus inactivation: The whole eyeball in sealed preservation may be transferred to a container of a constant temperature of −20° C. and irradiated with γ-ray at an irradiation dose of 25 kGy.

Step V. Crosslinking: The whole eyeball after irradiation may be transferred to a crosslinking agent solution containing 20% to 80% glycerol, and preserved at a temperature of 4° C. for 1 to 72 hours. The crosslinking agents may be 1-ethyl-3 -(3 -dimethylaminopropyl) carbodiimide (EDC) and N-Hydroxysulfosuccinimide (NHS) with a mass ratio of 1:1 to 3:1 and the final EDC concentration was 1.0% to 10.0% in the solution.

Step VI. Graft preparation: The whole eyeball after crosslinking may be taken out and washed twice with Ringer's solution for 5 minutes each time. Then, the whole eyeball may be cut along a line behind and 2 mm away from a corneal limbus of the eyeball to obtain a corneal sheet, then the corneal sheet may be placed in a lamellar cortical cutter that conducts cornea cutting at a thickness of 200 to 550 μm.

The method for preparing heterogenetic corneal material according to the present disclosure has four particular characteristics The first characteristic is the use of whole eyeball in preservation, which has the following advantages: (1) in Step III, the whole eyeball preservation effectively preserves the three-dimensional structure of corneal collagen fibers and the inherent morphology of natural cornea, and the glycerol dehydration process of cornea becomes more mild, slower, and more evenly, so that the three-dimensional structure of collagen fibers is protected from disruption of fast and intense dehydration; (2) in Step V, i.e., the whole eyeball crosslinking step, the eyeball is not dehydrated during preservation in glycerol of a certain concentration, effectively maintaining the original shape, thickness, and curvature of the cornea, with the structure and arrangement of the corneal collagen fibers being most similar to a fresh cornea. Crosslinking of a whole eyeball in this state can facilitate effective control of the speed and intensity of crosslinking. Slow and eveneven crosslinking under conditions closest to the natural morphology of the cornea is allowed. Therefore, corneal morphology and conformation of collagen fibers can be effectively preserved. For these reasons above, the whole eyeball preservation herein may provide corneal morphology and conformation of collagen fibers that are closer to a fresh cornea, resulting in a more transparent cornea lamellar material.

The second characteristic is the use of glycerol in the preservation, irradiation and crosslinking. A high concentration of glycerol (85% to 95% in concentration, the remaining 5% to 15% being a buffer solution) may be used in Step III, which has the following advantages: (1) first of all, glycerol itself is a cryoprotectant that can protect tissues and cells from damage caused by ice crystals during freezing and thawing and effectively prevents corneal collagen fibers from the influences of freezing and thawing. In addition, glycerol is non-cytotoxic, low in molecular weight, soluble in water, and easily eluted; (2) glycerol is strong in water absorption and thus able to effectively dehydrate corneal collagen. The best way for collagen preservation is dehydration. Compared with conventional freeze-drying process, high-concentration glycerol has a similar effect of dehydration. It can effectively maintain the morphology of corneal collagen, inactivating corneal epithelial cells, stromal cells, and endothelial cells, reducing immune responses triggered by the cells. As a result of the reasons above, the present method using glycerol with dehydration effects has benefits that far exceed the freeze-drying method; (3) glycerol also has antibacterial and virus inactivating effect, It has been reported that the virus inactivating effect of glycerol is positively correlated to glycerol concentration and duration of preservation. Preservation with 85% glycerol for 2 weeks can inactivate animal DNA virus and RNA virus. Therefore, preservation with >85% glycerol for more than 4 weeks according to the present disclosure can effectively inactivate viruses, so that the heterogenetic corneal material becomes safer; (4) glycerol can protect collagen fibers. It is known that γ-rays can severely damage collagen fibers and cause conformational changes in collagen fibers. Although 25 kGy γ-ray can effectively inactivate bacteria and viruses, as commonly known, such intensity of ray irradiation can cause extremely serious damage to the corneal collagen fibers. The present disclosure, by using glycerol for preservation, effectively prevents damage of high-intensity γ-ray to corneal collagen fibers and makes the corneal material more transparent at the same time; (5) the use of glycerol of medium concentration which absorbs water helps effectively avoid swelling of the corneal collagen during the crosslinking process thereof. Swelling may cause the diameter of corneal collagen fibers and the gaps among them to increase, leading to corneal opacity. This is because corneal transparency is highly correlated to collagen fiber diameter and gaps between the fibers. Higher degree of swelling makes the linkages between collagen fibers break more easily, Corneal edema is difficult to recover. Moderate concentrations of glycerol can effectively limit swelling and maintain a consistent thickness of the cornea. It helps the collagen fibers remain similar to those of a fresh cornea in the gaps between fibers during crosslinking, increases the molecular force between collagen fibers, and effectively protects the three-dimensional structure of collagen. As a result, the edema after transplantation is shortened in duration and also alleviated, and the cornea graft is thus more transparent.

The third characteristic is that the crosslinking agents chosen are 1-ethyl-3 3-dimethylaminopropyl) carbodiimide (EDC) and N-Hydroxysulfosuccinimide (NHS). They allow slow crosslinking within and among the corneal collagen fibers. Such crosslinking agents are also very mild in nature. The remaining water-soluble isourea as a product of the crosslinking reaction of collagen is easily eluted. In addition, the whole eyeball crosslinking allows a more gentle crosslinking process and slower penetration of the crosslinking agents into the corneal collagen fiber itself and the corneal collagen fiber matrix, enabling even and complete crosslinking of the tissue.

The fourth characteristic is that compared with the prior art, the present method disclosed herein is relatively simple, low in cost, easy to operate, and easy for industrial application.

DETAILED DESCRIPTION OF THE INVENTION

Embodiments of the present disclosure will be described below in further details for illustrative purpose only, but the embodiment of the present disclosure is not limited thereto.

Example 1

(1) Preparation: Porcine eyeballs were obtained within 2 hours after the death of a pig. The whole eyeball was washed with 2% povidone-iodine and 0.9% saline solution in sequence. Then, fascia muscles around the eyeball were cut off, and the whole eyeball was washed again with 2% povidone-iodine and 0.9% saline solution in sequence.

(2) Sterilization: The whole eyeball was immersed into 10 ml 50% high-glucose solution containing 40 mg of tobramycin for at least 20 minutes and then washed with at 0.9% saline.

(3) Cell inactivation: The eyeball in whole was immerged into a container containing a solution for sealed preservation, gradually cooled at a temperature drop rate of 2 to 3° C./min, and eventually subjected to long-term preservation at a temperature of −78° C. for 8 weeks. The preserving solution comprised 95% sterilizing glycerol and 5% buffer solution, wherein the buffer solution was a phosphate buffer solution.

(4) Virus inactivation: The whole eyeball in sealed preservation was transferred to a container of a constant temperature of −20° C., and irradiated with γ-ray at an irradiation dose of 25 kGy.

(5) Crosslinking: After thawing of the preserving solution, the eyeball was transferred to a crosslinking agent solution containing 80% glycerol, and preserved at a temperature of 4° C. for 48 hours. The crosslinking agent solution was consisted of 1-ethyl-3-(3-dimethylarninopropyl) carbodiimide (EDC) and N-Hydroxysulfosuccinimide (NHS) with a mass ratio of 3:1, wherein the final EDC concentration was 10.0% in the crosslinking agent solution. (It is important to note here that the crosslinking agent herein may be an inner or outer crosslinking agent. There are various types of crosslinking agents and experiments show that optimal results were obtained when 1-ethyl-3-(3-dimethylaminopropyl) carbodiimide (EDC) and N-Hydroxysulfosuccinimide (NHS) were used in combination with glycerol to prepare corneal materials).

(6) Graft preparation: The whole eyeball after crosslinking was taken out and washed twice with Ringer's solution for 5 minutes each time. Then, the whole eyeball was cut along a line behind and 2 mm away from a corneal limbus of the eyeball to obtain a corneal sheet. Then the corneal sheet was placed in a lamellar corneal cutter that conducts cornea cutting at a thickness of 200 μm. The graft was used in a keratoplasty experiment in rabbit.

(7) Animal Preparation: New Zealand White Rabbits weighing 2.5 to 3.0 kg were selected. Anesthetization was performed with 3% sodium pentobarbital (1 ml/kg, i.e., 30 mg/g) and Sumianxin 11 (0.25 ml/kg).

(8) Lamellar keratoplasty: A 7.5 mm corneal trephine was used to remove the lamellar sheets at a depth of about ⅔ of the corneal thickness. A 7.75 mm corneal trephine was employed to prepare the heterogenetic corneal graft. The heterogenetic corneal graft was transplanted in the corneal recipient bed by apposition suture. Corneal graft transparency and presence of rejection reaction were observed at one day, one week, eight weeks, and six months post surgery.

Example 2

(1) Preparation: Porcine eyeballs were obtained within 2 hours after the death of a pig. The whole eyeball was washed with 2% povidone-iodine and 0.9% saline solution in sequence. Then, fascia muscles around the eyeball were cut off, and the whole eyeball was washed again with 2% povidone-iodine and 0.9% saline solution in sequence.

(2) Sterilization: The whole eyeball was immersed into 10 ml 50% high-glucose solution containing 40 mg of tobramycin for at least 20 minutes and then washed with at 0.9% saline.

(3) Cell inactivation: The eyeball in whole was immersed into a container with glycorel solution for sealed preservation, gradually cooled at a temperature drop rate of 2 to 3° C./min, and eventually subjected to long-term preservation at a temperature of −78° C. for 10 weeks. The preserving solution comprised 90% sterilizing glycerol and 10% buffer solution, wherein the buffer solution was a phosphate buffer solution.

(4) Virus inactivation: The whole eyeball in sealed preservation was transferred to a container of a constant temperature of −20° C., and irradiated with γ-ray at an irradiation dose of 25 kGy.

(5) Crosslinking: After thawing the preserving solution, the eyeball was transferred to a crosslinking agent solution containing 50% glycerol, and preserved at a temperature of 4° C. for 48 hours. The crosslinking agent solution was consisted of 1-ethyl-3-(3-dimethylaminopropyl) carbodiimide (EDC) and N-Hydroxysulfosuccinimide (NHS) with a mass ratio of 2:1, wherein the final EDC concentration was 10.0% in the crosslinking agent solution. (It is important to note here that the crosslinking agent herein may be an inner or outer crosslinking agent solution. There are various types of crosslinking agents and experiments show that optimal results were obtained when 1-ethyl-3-(3-dimethylaminopropyl) carbodiimide (EDC) and N-Hydroxysulfosuccinimide (NHS) were used in combination with glycerol to prepare corneal materials).

(6) Graft preparation: The whole eyeball after crosslinking was taken out and washed twice with Ringer's solution for 5 minutes each time. Then, the whole eyeball was cut along a line behind and 2 mm away from a corneal limbus of the eyeball to obtain a corneal sheet; the corneal sheet was then placed in a lamellar corneal cutter that conducts cornea cutting at a thickness of 200 μm The graft was used in a keratoplasty experiment in rabbit.

(7) Animal Preparation: New Zealand White Rabbits weighing 2.5 to 3.0 kg were selected. Anesthetization was performed with 3% sodium pentobarbital (1 ml/kg, i.e., 30 mg/kg) and Sumianxin II (0.25 ml/kg).

(8) Lamellar keratoplasty: A 7.75 mm corneal trephine was used to remove the lamellar sheets at a depth of about 7/12 of the corneal thickness. An 8.00 mm corneal trephine was employed to prepare the heterogenetic corneal graft. The heterogenetic corneal graft was transplanted in the corneal recipient bed by apposition suture. Corneal graft transparency and presence of rejection reaction were observed at one day, one week, eight weeks, and six months post surgery.

Example 3

(1) Preparation: Porcine eyeballs were obtained within 2 hours after the death of a pig. The whole eyeball was washed with 2% povidone-iodine and 0.9% saline solution in sequence. Then, fascia muscles around the eyeball were cut off, and the whole eyeball was washed again with 2% povidone-iodine and 0.9% saline solution in sequence.

(2) Sterilization: The whole eyeball was immersed into 10 ml 50% high-glucose solution containing 40 mg of tobramycin for at least 20 minutes and then washed with at 0.9% saline.

(3) Cell inactivation: The eyeball in whole was immersed into a container with glycorel solution for sealed preservation, gradually cooled at a temperature drop rate of 2 to 3° C./min, and eventually subjected to long-term preservation at a temperature of −78° C. for 12 weeks. The preserving solution comprised 85% sterilizing glycerol and 15% buffer solution, wherein the buffer solution was a saline solution, (4) Virus inactivation: The whole eyeball in sealed preservation was transferred to a container of a constant temperature of −20° C., and irradiated with γ-ray at an irradiation dose of 25 kGy.

(5) Crosslinking: After thawing the preserving solution, the eyeball was transferred to a crosslinking agent solution containing 20% glycerol, and preserved at a temperature of 4° C. for 48 hours. The crosslinking agent solution was consisted of 1-ethyl-3-(3-dimethylaminopropyl) carbodiimide (EDC) and N-Hydroxysulfosuccinimide (NHS) with a mass ratio of 1:1, wherein the final EDC concentration was 1.0% in the crosslinking agent solution.

(6) Graft preparation: The whole eyeball after crosslinking was taken out and washed twice with Ringer's solution for 5 minutes each time. Then, the whole eyeball was cut along a line behind and 2 mm away from a corneal limbus of the eyeball to obtain a corneal sheet, the corneal sheet was then placed in a lamellar corneal cutter that conducts cornea cutting at a thickness of 150 μm. The graft was used in a keratoplasty experiment in rabbit.

(7) Animal Preparation: New Zealand White Rabbits weighing 2.5 to 3.0 kg were selected. Anesthetization was performed with 3% sodium pentobarbital (1 ml/kg, i.e., 30 mg/kg) Sumianxin II (0.25 ml/kg).

(8) Lamellar keratoplasty: A 10.0 mm corneal trephine was used to conduct intralamnellar dialdysis of cornea at a depth of about ½ of the cornea thickness in the direction of 12 o'clock. A 5.5 mm-sized heterogenetic corneal graft was inserted in interlayer. Corneal graft transparency and presence of rejection reaction were observed at one day, one week, eight weeks, and six months post surgery.

By preparing the corneal material according to this disclosure, the corneal collagen fiber structure can be preserved, and transparency of the corneal material can be significantly improved after transplantation. Such corneal materials prepared as disclosed herein thus can be widely used in the medical field.

The invention claimed is:

1. A method for preparing a heterogenetic corneal material, comprising the steps of:
   (1) inactivating cells: obtaining an eyeball that can be used as a heterogenetic corneal material from a dead animal,
   (a) immerging the eyeball in whole into a solution under sealed conditions, wherein the solution comprises 85% to 95% of glycerol and 5% to 15% of a buffer solution,
   (b) cooling the solution with the eyeball at a temperature drop rate of 2 to 3 ° C/min to a temperature of −78° C., and
   (c) preserving the eyeball in solution by maintaining both at a temperature of −78° C. for a duration of at least four weeks, (2) inactivating virus: transferring the eyeball preserved under the sealed conditions in step (1) to a container of a constant temperature of −20° C., and irradiating the container containing the eyeball with γ-rays at an irradiation dose of 25 kGy;

(3) crosslinking: transferring the eyeball from step (2) to a crosslinking agent solution comprising 20% to 80% glycerol, and preserving the same at a temperature of 4° C. for 1 to 72 hours; and (4) preparing a graft: cutting the eyeball from step (3) along a line behind and 2 mm away from corneal limbus to obtain a corneal sheet, and placing the corneal sheet in a lamellar corneal cutter that conducts cornea cutting at a thickness of 200 to 550 μm.

2. The method for preparing a heterogenetic corneal material according to claim 1, wherein the crosslinking agent solution is consisted of 1-ethyl-3-(3-dimethylaminopropyl) carbodiimide (EDC) and N-Hydroxysulfosuccinimide (NHS) with a mass ratio of 1: 1 to 3: 1 and final EDC concentration of 1.0% to 10.0% in the crosslinking agent solution.

3. The method for preparing a heterogenetic corneal material according to claim 1, wherein the eyeball is obtained within four hours after death of the dead animal; and wherein, before immerging the eyeball in whole into a solution under sealed conditions, the eyeball is washed with 2% povidone-iodine and 0.9% saline solution in sequence, fascia muscles around the eyeball are cut off, and the eyeball is washed again with 2% povidone-iodine and 0.9% saline solution in sequence.

4. The method for preparing a heterogenetic corneal material according to claim 3, wherein before immerging the eyeball in whole into a solution under sealed conditions, the eyeball is further immerged into 50% high-glucose solution containing 40 mg of tobramycin for at least 20 minutes and then washed with 0.9% saline.

5. The method for preparing a heterogenetic corneal material according to claim 1, wherein, before cutting along a line behind and 2 mm away from a corneal limbus of the eyeball, the eyeball is washed twice with Ringer's solution for 5 minutes each time.

6. A method for preparing a heterogenetic corneal material, comprising the steps of:

(1) inactivating cells: obtaining an eyeball that can be used as a heterogenetic corneal material from a dead animal,
   (a) immerging the eyeball in whole into a solution under sealed conditions, wherein the solution comprises 85% to 95% of glycerol and 5% to 15% of a buffer solution,
   (b) cooling the solution with the eyeball at a temperature drop rate of 2 to 3 ° C/min to a temperature of −78° C., and
   (c) preserving the eyeball in solution by maintaining both at a temperature of −78° C. for a duration of at least four weeks, (2) inactivating virus: transferring the eyeball preserved under the sealed conditions in step (1) to a container of a constant temperature of −20° C., and irradiating the container containing the eyeball with γ-rays at an irradiation dose of 25 kGy;

(3) crosslinking: transferring the eyeball from step (2) to a crosslinking agent solution comprising 20% to 80% glycerol, and preserving the same at a temperature of 4° C. for 1 to 72 hours, wherein the crosslinking agent solution is consisted of 1-ethyl-3-(3-dimethylaminopropyl) carbodiimide (EDC) and N-Hydroxysulfosuccinimide (NHS) with a mass ratio of 1:1 to 3:1 and final EDC concentration of 1.0% to 10.0% in the crosslinking agent solution; and (4) preparing a graft: cutting the eyeball from step (3) along a line behind and 2 mm away from corneal limbus to obtain a corneal sheet, and placing the corneal sheet in a lamellar corneal cutter that conducts cornea cutting at a thickness of 200 to 550 μm.

\* \* \* \* \*